United States Patent
Pacchetti

(10) Patent No.: US 10,251,820 B2
(45) Date of Patent: Apr. 9, 2019

(54) TOPICAL COMPOSITION COMPRISING PLANT EXTRACTS

(71) Applicant: LINNEA SA, Riazzino (CH)

(72) Inventor: Barbara Pacchetti, Riazzino (CH)

(73) Assignee: LINNEA S.A., Riazzino (Locarno) (CH)

( * ) Notice: Subject to any disclaimer, the term of this patent is extended or adjusted under 35 U.S.C. 154(b) by 0 days.

(21) Appl. No.: 15/475,834

(22) Filed: Mar. 31, 2017

(65) Prior Publication Data
US 2017/0281481 A1 Oct. 5, 2017

(30) Foreign Application Priority Data
Apr. 1, 2016 (IT) .................. 102016000033595

(51) Int. Cl.

| | | |
|---|---|---|
| A61K 8/04 | (2006.01) | |
| A61K 8/14 | (2006.01) | |
| A61K 8/97 | (2017.01) | |
| A61K 9/00 | (2006.01) | |
| A61K 9/107 | (2006.01) | |
| A61K 36/15 | (2006.01) | |
| A61K 36/16 | (2006.01) | |
| A61K 36/45 | (2006.01) | |
| A61K 36/48 | (2006.01) | |
| A61Q 7/00 | (2006.01) | |
| A61Q 17/00 | (2006.01) | |
| A61Q 19/00 | (2006.01) | |
| A61Q 19/08 | (2006.01) | |
| B01J 13/04 | (2006.01) | |
| A61K 8/58 | (2006.01) | |
| A61K 8/894 | (2006.01) | |
| A61K 47/10 | (2017.01) | |
| A61K 47/24 | (2006.01) | |
| A61K 9/06 | (2006.01) | |
| A61K 9/10 | (2006.01) | |
| A61K 47/44 | (2017.01) | |
| A61K 9/127 | (2006.01) | |
| A61K 8/06 | (2006.01) | |

(52) U.S. Cl.
CPC .............. *A61K 8/14* (2013.01); *A61K 8/042* (2013.01); *A61K 8/062* (2013.01); *A61K 8/585* (2013.01); *A61K 8/894* (2013.01); *A61K 8/97* (2013.01); *A61K 9/0014* (2013.01); *A61K 9/0034* (2013.01); *A61K 9/06* (2013.01); *A61K 9/10* (2013.01); *A61K 9/107* (2013.01); *A61K 9/1272* (2013.01); *A61K 36/15* (2013.01); *A61K 36/16* (2013.01); *A61K 36/45* (2013.01); *A61K 36/48* (2013.01); *A61K 47/10* (2013.01); *A61K 47/24* (2013.01); *A61K 47/44* (2013.01); *A61Q 7/00* (2013.01); *A61Q 17/005* (2013.01); *A61Q 19/00* (2013.01); *A61Q 19/08* (2013.01); *B01J 13/046* (2013.01); *A61K 2800/5922* (2013.01)

(58) Field of Classification Search
USPC ........................................................ 424/450
See application file for complete search history.

(56) References Cited

U.S. PATENT DOCUMENTS

2011/0229538 A1* 9/2011 Matravers et al. ...... A61K 8/97
424/401

FOREIGN PATENT DOCUMENTS

| KR | 20020065958 | * | 8/2002 |
| KR | 20020065958 A | * | 8/2002 |

OTHER PUBLICATIONS

Madhav et al., "Niosomes: a novel drug delivery system"; International Journal of Research in Pharmacy and Chemistry, IJRPC 2011, 1(3), pp. 498-511.
J.Pinnagoda et al., "Guidelines for tamepidermal water loss (TEWL) measurement", Standardization Group of the European Society of Contact Dermatitis 1990; vol. 22, pp. 164-178.
Muinoff SC, Turner MLC, Vulvar vestibulitis syndrome, Dermatol clin 1992;10;(2): 435-44.
USP 1724 (2015) SemiSolid Drug Product—Performance Tests, 2055.

* cited by examiner

*Primary Examiner* — Nannette Holloman
(74) *Attorney, Agent, or Firm* — Oblon, McClelland, Maier & Neustadt, L.L.P.

(57) ABSTRACT

The present invention relates to a topical composition comprising plant extracts. In particular, the present invention relates to a topical composition comprising plant extracts embedded in hydrophilic vesicles (niosomes), preferably having a size smaller than 500 nm, and at least one topically acceptable excipient.

18 Claims, 1 Drawing Sheet

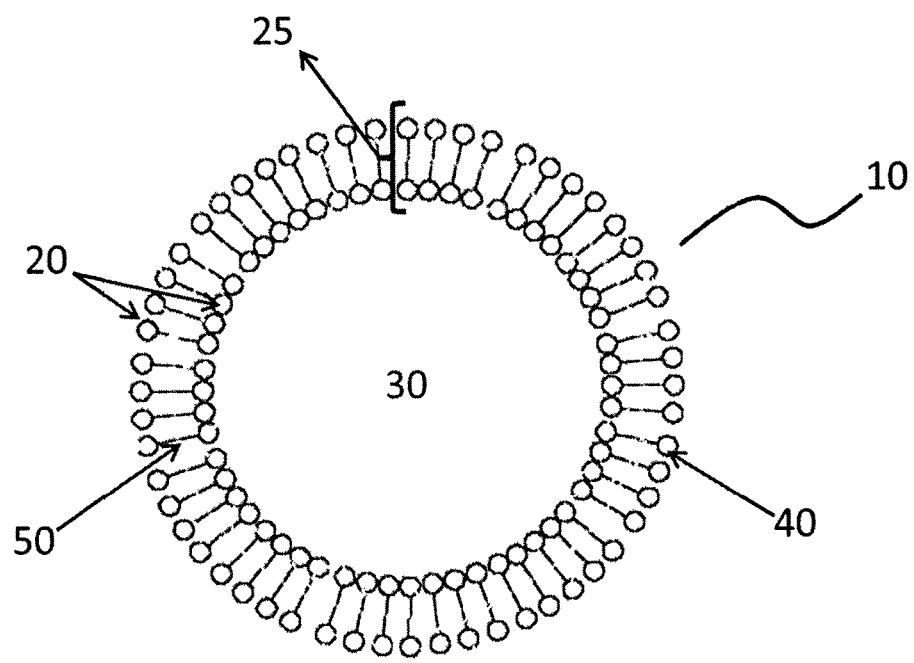

TOPICAL COMPOSITION COMPRISING PLANT EXTRACTS

FIELD OF THE INVENTION

The present invention relates to a topical composition comprising plant extracts. In particular, the present invention relates to a topical composition comprising plant extracts embedded in hydrophilic vesicles (niosomes), preferably having a size smaller than 500 nm, and at least one topically acceptable excipient.

PRIOR ART

Plant extracts are liquid compositions (fluid extracts), solid compositions (dry extracts) or compositions of intermediate consistency (soft extracts), prepared from fresh or dried plant parts (leaves, flowers, roots, and so on), by extracting with a suitable solvent (water, alcohol, acetone, and so on).

Dry plant extracts are in the form of powder preparations, and are obtained by complete evaporation of the solvent. Dry extracts usually have a dry residue not less than 95% by weight.

Plant extracts are widely known for use in Pharmacopoeia, where they are used for their therapeutic properties. Among these, we may mention, as examples, anthocyanin extracts, such as those of bilberry, isoflavone extracts, such as those of red clover, extracts of lignans such as those of Norway spruce, terpene extracts such as those of *ginkgo biloba* and of centella asiatica, extracts of alkaloids and polyphenols, such as those of sweet clover, of lemon balm, of passion flower and of guarana, and extracts of bioflavonoids (rutin and quercetin, also in their glycosidic form).

Extracts of Norway spruce, for their high content of lignans, find application in the prevention of inflammatory diseases associated with oxidative stress, of cardiovascular diseases, and for preventing or alleviating the symptoms connected with deficiency of oestrogens, particularly in a menopausal woman.

The dried fruits of bilberry have astringent properties and can be used as antidiarrhoeal agents. Some of the substances present in the fruit have been shown to be useful for the blood circulation, for the functionality of the microcirculation and for the eyes, also in the presence of degenerative diseases such as diabetes. In particular, the effects of the anthocyanins on the capillaries of the retina are emphasized, as they can protect the walls of the capillary vessels and exert a beneficial action on the microcirculation, and in vascular problems and trophism of the vascular endothelium.

The dry extract obtained from the leaves of the *ginkgo biloba* plant has been used in medicine since about the middle of last century in treatments associated with cerebral disorders and with impairments of the peripheral circulation. *Ginkgo biloba* extract may potentially be used in the treatment of neurodegenerative disorders, in particular it has beneficial effects on dysfunctions associated with Alzheimer's disease and with senile dementia. Moreover, it is found to be useful in cardiovascular disorders (especially in reduction of platelet adhesion), at the level of the neurosensory system (especially in protection of the retina) and more generally in cardiac and peripheral endothelial vasodilation.

Red clover dry extract is used essentially in the prevention and/or treatment of the symptoms and risk factors connected with menopause and post-menopause. This is due to its high content of isoflavones, which mimic the structure and behaviour of the oestrogens but without the side-effects caused by hormone replacement therapy.

It is known that plant extracts, especially dry extracts, are scarcely suitable for topical formulations, especially cosmetic products and/or medical devices for applications on the skin and on the mucosae, because of their usual insolubility in water, their rather unsuitable colour for cosmetic matrices which are usually white, their sensitivity to pH and/or its variations during the procedures for preparation and storage, and their instability or incompatibility with the high percentage of water usually present in a cream, lotion, gel or other topical formulation.

SUMMARY OF THE INVENTION

The applicant has perceived the interest in incorporating plant extracts in topical compositions, particularly cosmetics and/or medical devices, for applications on the skin and on the mucosae.

The applicant therefore has faced the problem of making a topical composition comprising plant extracts that overcomes the aforementioned disadvantages and drawbacks.

In particular, the applicant has faced the problem of making a topical composition comprising plant extracts in the form of a water-based emulsion that is stable over time and that does not give rise to phenomena of separation and/or precipitation and/or alteration of its components.

At the same time, the applicant has faced the problem of making a topical composition comprising plant extracts that has a pleasant appearance and coloration and is not subject to colour changes during preparation and over time.

In particular, the applicant has faced the problem of incorporating concentrated and high-titre plant extracts of Norway spruce, red clover, *ginkgo biloba* and bilberry in topical compositions.

The applicant has surprisingly found that plant extracts could be embedded in hydrophilic vesicles (niosomes), preferably having a size smaller than 500 nm, obtaining an aqueous solution/dispersion that is stable and colourless.

The applicant has also surprisingly found that the aqueous solution/dispersion comprising niosomes of plant extracts could be used for preparing water-based topical compositions, in particular waters, micellar waters, emulsions, lotions, balms, creams and gels, which are stable over time and do not have particular colorations.

Moreover, the applicant has found, surprisingly, that the topical compositions obtained by incorporating the niosomes of plant extracts had unexpected hydrating, anti-ageing and anti-wrinkle properties when applied on the skin, in addition displaying trophic and hydrating properties when applied to the mucosae, especially the vaginal mucosae.

The applicant has observed that the water-based composition of plant extracts embedded in hydrophilic vesicles (niosomes) showed properties of absorption of the active principles through the skin that were surprisingly higher compared to those of the base plant extract incorporated in glycerine.

The applicant has found, unexpectedly, that the topical compositions obtained by incorporating the niosomes of plant extracts of Norway spruce had a surprising anti-irritant and calming effect on skin that is sensitive to inflammatory or irritant phenomena.

The applicant has observed, moreover, that the topical compositions obtained by incorporating the niosomes of plant extracts of red clover were surprisingly effective in preventing or reducing the dyschromia and loss of uniformity of the complexion colour typical of ageing.

The applicant has also observed that the topical compositions obtained by incorporating the niosomes of plant extracts of *ginkgo biloba* were surprisingly effective in stimulating the peripheral circulation.

Finally, the applicant has observed that the topical compositions obtained by incorporating the niosomes of plant extracts of bilberry were surprisingly effective in reducing the redness and oedema associated with the microcirculation of the cutaneous compartment.

Consequently, a first aspect of the present invention relates to a topical composition comprising a water-based composition of plant extracts embedded in hydrophilic vesicles (niosomes) having a size smaller than 500 nm, and at least a topically acceptable excipient.

A second aspect of the present invention relates to a water-based composition, in particular an aqueous dispersion or solution, comprising plant extracts embedded in hydrophilic vesicles (niosomes), where said plant extracts are preferably selected from the group consisting of plant extracts of Norway spruce, red clover, *ginkgo biloba* and bilberry.

More particularly, the present invention relates to a water-based composition comprising plant extracts embedded in hydrophilic vesicles (niosomes), where said hydrophilic vesicles comprise esters of linear or branched polyglycerols with saturated or monounsaturated linear fatty acids.

A third aspect of the present invention relates to a method for preparing a water-based composition comprising hydrophilic vesicles (niosomes) containing plant extracts comprising the use of techniques of hand shaking or with ultrasound.

BRIEF DESCRIPTION OF THE DRAWINGS

The present invention will be better illustrated in the following detailed description, presented below with reference to the appended drawings, supplied only for guidance, and therefore non-limiting, in which:

FIG. 1 shows schematically a section of a niosome (10) and provides a representation of the orientation of the surfactant molecules (20), where the dot represents the hydrophilic end (40) and the line represents the hydrophobic end (50), to form a double-layer monolamellar structure (25) that encloses an aqueous compartment (30).

DETAILED DESCRIPTION OF THE INVENTION

In a first aspect, the present invention relates to a topical composition comprising a water-based composition of plant extracts embedded in hydrophilic vesicles (niosomes) of substantially spherical shape having a diameter lower than 500 nm, and at least a topically acceptable excipient.

The expression "topically acceptable" used in the present description is intended to define substances that are recognized to be free from adverse side-effects (irritation, toxicity, and so on) if applied on the skin and/or on the mucosae.

Advantageously, the niosomes used in the present invention have a diameter lower than 400 nm, more preferably lower than 300 nm, and even more preferably lower than 200 nm.

Preferably, the niosomes used in the present invention have a diameter greater than 10 nm, more preferably greater than 20 nm, and even more preferably greater than 40 nm.

Advantageously, the niosomes used in the present invention have a diameter of from 50 nm to 180 nm, preferably of from 70 nm to 150 nm.

The plant extracts preferably used in the present invention are selected from the group consisting of plant extracts of Norway spruce, red clover, *ginkgo biloba* and bilberry.

Referring to FIG. 1, the niosomes (10) used for the purposes of the present invention are non-ionic hydrophilic vesicles formed by a double layer of amphiphilic molecules (20) that surround an aqueous compartment (30).

In particular, the amphiphilic molecules used for forming the niosomes used for the purposes of the present invention are non-ionic surfactants. The surfactant molecules tend to self-organize in a double-layer monolamellar structure (25) in such a way that the hydrophilic ends (40) of the non-ionic surfactant point towards the exterior of the lamella, while the hydrophobe ends (50) face one another inside the lamellae to form the double layer (20), as illustrated in FIG. 1.

The plant extracts are embedded in the aqueous compartment (30) delimited by the double layer of amphiphilic molecules (20) that forms the non-ionic hydrophilic vesicles (10). In this way, the plant extracts can be transported and maintained in dispersion/solution in an aqueous medium, in particular in the water-based composition of the present invention.

The surfactants that are particularly preferred for producing the niosomes used for the purposes of the present invention consist of esters of linear or branched polyglycerols, with saturated or monounsaturated linear fatty acids, or mixtures thereof.

Useful examples of linear or branched polyglycerols are represented by the following general formulae (I) and (II):

$$H-(OCH_2-CHOH-CH_2)_n-OH \quad (I)$$

$$H-(OCH_2-CH(CH_2OH))_n-OH \quad (II)$$

where n is an integer from 2 to 10.

Preferred examples of polyglycerols represented by general formulae (I) and (II) are triglycerol, tetraglycerol, hexaglycerol, octaglycerol, and decaglycerol.

The linear or branched polyglycerols suitable for the present invention are commercially available. Examples of commercial products are the polyglycerols distributed with the trade name Vegetable Polyglycerine-3, Vegetable Polyglycerine-4, Vegetable Polyglycerine-6, and Vegetable Polyglycerine-10 by the company Spiga Nord S.p.A., and with the trade name Polyglycerol-3 and Polyglycerol-4 by the company Solvay Chemicals, Inc.

Useful examples of saturated linear fatty acids comprise monocarboxylic acids having from 4 to 32 carbon atoms, such as butyric acid, valeric (valerianic) acid, caproic acid, enanthic acid, caprylic acid, pelargonic acid, capric acid, lauric acid, myristic acid, palmitic acid, margaric acid, stearic acid, arachidic acid, behenic acid, lignoceric acid, cerotic acid, montanic acid, melissic acid, and laceroic acid.

Preferred saturated linear fatty acids comprise monocarboxylic acids having from 12 to 22 carbon atoms, such as lauric acid, myristic acid, palmitic acid, margaric acid, stearic acid, arachidic acid, and behenic acid.

Useful examples of monounsaturated linear fatty acids comprise monocarboxylic acids having from 14 to 24 carbon atoms, for example myristoleic acid, palmitoleic acid, oleic acid, gadoleic acid and erucic acid.

Useful examples of mixtures of fatty acids are represented by the vegetable oils obtainable by pressing or extracting seeds or fruits, for example olive oil, peanut oil, coconut oil, palm oil, and colza oil. Olive oil and coconut oil are preferred, and in particular olive oil, for the reduced content of polyunsaturated acids.

The esters of linear or branched polyglycerols with saturated or monounsaturated linear fatty acids useful in the present invention may be represented by the following general formula:

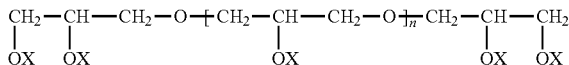

where n is an integer from 0 to 8 and the residue X represents a hydrogen atom or an acyl group R—CO—, where R is a saturated or monounsaturated alkyl chain comprising from 3 to 31 carbon atoms, preferably from 11 to 21 carbon atoms, and where at least one and not more than three, preferably one or two, of said residues X are represented by said acyl group R—CO—.

The esters of linear or branched polyglycerols with saturated or monounsaturated linear fatty acids, or mixtures thereof, useful in the present invention are commercially available. Examples of commercial products are the polyglycerol esters produced and distributed by the company Naturalis s.r.l. with the trade name Soavirol, for example Soavirol OV6 (olive oil polyglyceryl-6 ester), Soavirol OV4 (olive oil polyglyceryl-4 ester), and by the company Nikko Chemicals Co., Ltd. with the trade name Nikkol Hexaglyn, for example Nikkol Hexaglyn 1-L (polyglyceryl-6 laurate) and Nikkol Hexaglyn PR-15 (polyglyceryl-6 polyricinoleate).

In the production of the niosomes used for the purposes of the present invention, preferably further components are used that are suitable for stabilizing and preserving the aqueous solution/dispersion of niosomes, such as for example glycerin and water-soluble natural antioxidants such as ascorbic acid and derivatives thereof, isoflavones, magnolol, tetrahydromagnolol, honokiol, and obovatol.

In particular, the plant extracts used for producing the topical composition of the present invention are plant extracts of Norway spruce, red clover, *ginkgo biloba* and bilberry.

7-Hydroxymatairesinol (HMR) is the single component of the lignans that is by far the most abundant in the extracts of Norway spruce (*Picea abies*), in which it reaches a concentration of about 60% by weight of the total lignans.

In the Norway spruce, the concentration of the lignans in the thick roots is 2-3 percent. An abundance of lignans is present in the heartwood of branches (5-10 percent) and branchings (twist), in particular in the knots, in which the amount of lignans may exceed 10 percent. These concentrations are about one hundred times those of ground linseed powder, known to be a material rich in lignans.

The HMR for use in this invention can be isolated from a fraction of fragments of large dimensions (containing branches, twists and knots) by compressing wood of Norway spruce (*Picea abies*). The whole extract of *Picea abies* (TEP, containing HMR and the isomer) and purified HMR, HMRLignan™ (containing mainly HMR) are available commercially from Linnea SA, Riazzino, Switzerland.

The bilberry (*Vaccinium myrtillus* L.) is a shrubby plant of the family Ericaceae. Bilberry extract, obtained from the dried fruits, as given in the European Pharmacopoeia, contains 36% of anthocyanosides, corresponding to 25% anthocyanidins, and other components such as flavonoids, catechins, polyphenols, sugars, pectins, tannins, vitamin A, C, and, in minor amounts, vitamin B.

*Ginkgo biloba* is a plant that is the only surviving species of the family Ginkgoaceae. *Ginkgo biloba* extract is obtained from various plant parts, but the extract used for medical purposes is mainly obtained from the leaves.

As stated in the European Pharmacopoeia, the dry extract obtained from the leaves of *ginkgo biloba* contains (i) from 22% to 27% by weight of flavonoids selected from the group comprising quercetin, campherol and glycosidic derivatives of isorhamnetin; (ii) from 2.8 to 3.4% by weight of ginkgolides A, B and C; (iii) from 2.6 to 3.2% by weight of biobalides; and (iv) not more than 5 ppm of ginkgolic acids.

Red clover (*Trifolium pratense*) is a perennial herbaceous plant, belonging to the family Fabaceae. Red clover extract is obtained from the leaves and/or from the red flowers that grow at the ends of the branches of the plant.

Red clover extract contains three classes of active principles: isoflavones, lignans and coumestrol. The major amount of active principle is represented by the isoflavones in aglyconic form, the only example in nature, and represented almost entirely by biochanin A and formononetin, while genistein and daidzein are present in smaller amounts. Lignans and coumestrol, instead, are present in very small amounts, and their contribution to the activity of red clover is almost insignificant. In particular, the extract used for the present invention is a red clover extract with a titre of 36-44% of total isoflavones, expressed as the sum of biochanin A, formononetin, genistein and daidzein.

The water-based composition comprising niosomes of the present invention may be prepared by the techniques known in the art, for example by the technique of manual agitation (hand shaking) or by the ultrasound technique.

Hand shaking comprises a first step of dissolving the components in a volatile organic solvent, for example ethyl ether, chloroform or methanol, carried out in a round-bottomed glass flask, a second step of evaporation, carried out in a rotary evaporator at room temperature (20-25° C.), which leaves a thin layer of the components deposited on the walls of the round-bottomed flask, and finally a third step of rehydration with an aqueous phase comprising the plant extracts at a temperature between 0° C. and 60° C., under gentle stirring.

The ultrasound technique comprises sonication, at a temperature between 0° C. and 60° C., of a dispersion obtained by mixing an organic phase comprising the surfactants and an aqueous phase comprising the plant extracts.

These and other methods for preparing compositions comprising niosomes are described in the literature, for example in the article by Madhav et al., "Niosomes: a novel drug delivery system"; International Journal of Research in Pharmacy and Chemistry, IJRPC 2011, 1(3), 498-511.

The resultant dispersion/solution of niosomes comprises water in an amount of from 30% to 40% by weight relative to the total weight of the dispersion/solution of niosomes.

The esters of polyglycerols constitute the major portion, of from 35% to 50% by weight relative to the total weight of the dispersion/solution of niosomes.

Glycerin is present in an amount of from 10% to 20% by weight relative to the total weight of the dispersion/solution of niosomes.

The plant extracts are included in a more limited amount, of from 2% and 5% by weight relative to the total weight of the dispersion/solution of niosomes.

The antioxidants represent the minor portion, of from 1% to 6% by weight relative to the total weight of the dispersion/solution of niosomes.

The topical composition of the present invention may be liquid or semisolid.

In particular, the topical composition of the present invention consists of a cosmetic composition and/or a medical device, for application on the skin and on the mucosae.

The topical composition of the present invention advantageously comprises liquid or semisolid compositions, in which the water-based composition of niosomes is dispersed in an amount of from 1% to 5% by weight relative to the total weight of the topical composition.

The liquid compositions of the present invention comprise solutions, emulsions, microemulsions, lotions, foams, milks, oils, foaming products or suspensions with a wide variation of viscosity.

The liquid compositions comprise, for example, aqueous solutions, aqueous-alcoholic solutions, oily solutions, emulsions obtained by dispersing an oily phase in an aqueous phase (oil-in-water) or, vice versa, an aqueous phase in an oily phase (water-in-oil), and suspensions, obtained by dispersing a dispersed phase, consisting of solid particles, in a dispersing medium generally represented by an aqueous or oily liquid of a certain viscosity.

The semisolid compositions of the present invention comprise creams, gels, balms, ointments, pastes, cream gels, sticks and waxes.

Moreover, the compositions for topical use of the present invention may comprise various topically acceptable additives or vehicles useful for preparing cosmetics and/or medical devices known by a person skilled in the art, for example emulsifiers, hydrating agents, solvents, emollients, stabilizers, viscosity modifiers, preservatives, lubricants, sequestering or chelating agents, fillers, powders, fragrances, perfumes, absorbents, dyes and opacifiers, antioxidants, vitamins, screening substances, UV filters, essential oils, keratin-active substances, and amino acids.

Suitable solvent additives comprise, for example, water, alcohols, ketones (such as acetone and methyl isobutyl ketone), glycols (such as ethylene glycol, propylene glycol and butylene glycol), polyethylene glycols (such as PEG-40, PEG-50, PEG-60), alkyl acetates (such as amyl acetate, isopropyl acetate, butyl acetate), paraffins and isoparaffins, cycloalkyls (such as cyclohexane), glycerin, natural and synthetic oils, natural and synthetic triglycerides.

Advantageously, the topical compositions of the present invention are aqueous compositions.

In the aqueous compositions, water represents the main component of the composition, even reaching an amount of up to 99% by weight relative to the total weight of the composition. The aqueous compositions contain an amount of water preferably of from 25% to 95% by weight, preferably of from 50% to 90% by weight relative to the total weight of the composition.

The aqueous compositions of the present invention may preferably comprise a total amount of non-aqueous solvents of from about 0.1% to about 60%, more preferably of from 1% to 40%, and even more preferably of from 5 to 35% by weight relative to the total weight of the composition.

Examples of suitable emulsifying additives are non-ionic, cationic, anionic and amphoteric surfactants, or a combination thereof. Examples of emulsifiers useful in the present invention are sorbitans, ethoxylated long-chain alcohols, alkyl polyglycosides, soaps, alkyl sulphates, such as, for example, cetylstearylsulphate sodium, monoalkyl and dialkyl phosphates, alkyl sulphonates, hydrogenated castor oil, acyl isethionates, sucrose esters, betaines, lecithins, quaternary ammonium salts, alkyl oleates, glycerides, such as, for example, caprylocaproyl polyoxyglycerides (caprylocaproyl macrogolglycerides) and emulsifying agents from olive oil.

Preferably, the composition of the present invention comprises a total amount of emulsifying agents of from about 0.1% to about 60%, more preferably of from 0.5% to 25%, and even more preferably of from 0.5% to 10% by weight relative to the total weight of the composition.

Typical viscosity modifying additives useful in the present invention are, for example, xanthan gum, hydroxypropylcellulose, hydroxyethylcellulose, Carbopol, carrageenans, poloxamers, and acacia gum.

Advantageously, the composition of the present invention comprises a total amount of viscosity modifiers of from about 0.1% to about 25%, more preferably of from 0.5% to 10%, and even more preferably of from 0.5% to 5% by weight relative to the total weight of the composition.

Examples of additives with hydrating action useful in the present invention are, for example, urea, allantoin, hyaluronic acid and derivatives thereof, glycerin, amino acids, acetyl monoethanolamides, butoxypropanol, butyl glycol, polyethylene glycols of low molecular weight (such as PEG-40, PEG-50, PEG-60), aloe, mallow, trehalose and sorbitol.

Preferably, the composition of the present invention comprises a total amount of hydrating agents of from about 0.05% to about 25%, more preferably of from 0.5% to 10%, and even more preferably of from 0.1% to 5% by weight relative to the total weight of the composition.

Examples of suitable emollients useful in the present invention include, for example, lanolin, almond oil, olive oil, hydrogenated castor oil, microcrystalline wax, polydimethylsiloxane (dimethicone), polymethylphenylsiloxane, polymers of glycol and silicone, mineral oils, paraffin, ozokerite, ceresin, triglyceride esters, monoglycerides acetylates, ethoxylated glycerides, alkyl esters of fatty acids, fatty acids, long-chain alcohols, sterols, beeswax, polyhydric alcohols, polyesters, and amides of fatty acids.

Preferably, the composition of the present invention comprises a total amount of emollients of from about 0.1% to about 25%, more preferably of from 0.5% to 10%, and even more preferably of from 0.5% to 5% by weight relative to the total weight of the composition.

Examples of suitable preservatives useful in the present invention include, for example, alcohols, such as ethanol, phenoxyethanol and benzyl alcohol, methyl and propyl parahydroxybenzoate, hydroxyanisole butylate (BHA), sorbates, urea derivatives, and isothiazolinones. Other examples of dyes usable in the topical composition of the present invention may be found in annex V of regulation (EC) No. 1223/2009 dated 30 Nov. 2009.

Preferably, the composition of the present invention comprises a total amount of preservatives of from about 0.01% to about 2.00%, more preferably of from 0.05% to 1.00%, and even more preferably of from 0.1% to 0.5% by weight relative to the total weight of the composition.

Examples of sequestering or chelating additives useful in the present invention are EDTA, HEDTA, alkyl oxalates, lithium or potassium oxalate, sodium or potassium pyrophosphate. Preferably, the composition of the present invention comprises a total amount of sequestering or chelating additives of from about 0.01% to about 20%, more preferably of from 0.05% to 10%, and even more preferably of from 0.1% to 5% by weight relative to the total weight of the composition.

Examples of suitable stabilizers useful in the present invention are long-chain alcohols (such as cetyl alcohol, stearyl alcohol) and mixtures thereof, polyethylene glycols of high molecular weight (such as PEG-9000 and PEG 14000) and polyvinyl pyrrolidones (such as povidone).

The composition of the present invention preferably comprises a total amount of stabilizers of from about 0.1% to about 25%, more preferably of from 0.5% to 15%, and even more preferably of from 1% to 10% by weight relative to the total weight of the composition.

Examples of suitable additives in powder form useful in the present invention are elastomeric silicones such as dimethicone/vinyldimethicone crosspolymers (DC 9506, Dow Corning), mixtures of cyclomethicone and dimethicone crosspolymers (DC 9040, Dow Corning), crosspolymers of dimethicone and vinyl dimethicone treated with silica (DC 9701, Dow Corning), mixtures of crosspolymers of cyclomethicone and dimethicone/vinyldimethicone (SFE 839, GE Bayer Silicones).

The composition of the present invention preferably comprises a total amount of additives in powder form of from about 0.1% to about 5%, more preferably of from 0.2% to 1% by weight, relative to the total weight of the composition.

Examples of opacifiers useful in the present invention are zinc or aluminium oxide, titanium or zinc dioxide, alumina, mica, salts of fatty acids with aluminium, and gypsum.

Examples of dyes preferably used in the present invention are easily washable water-soluble dyes that do not stain the skin and do not leave residues such as, for example, Acid Blue 3 C.I.42051, Acid Blue 9 C.I.42090, Acid Blue 74 C.I.73015, Pigment Blue 15 C.I.74160, Acid Yellow 3 C.I.47005, Food Yellow 3 C.I.15985, Acid Yellow 23 C.I.19140, Acid Yellow 73 C.I.45350, Acid Red 14 C.I.14720, Acid Red 18 C.I.16255, Acid Red 27 C.I.16185, Acid Red 51 C.I.45430, Acid Green 1 C.I.10020, Acid Green 25 C.I.61570, and mixtures thereof. Other examples of dyes usable in the topical composition of the present invention may be found in annex IV of the regulation (EC) No. 1223/2009 dated 30 Nov. 2009.

Preferably, the composition of the present invention comprises a total amount of opacifiers and dyes of from about 0.01% to about 15%, more preferably of from 0.05% to 5% by weight relative to the total weight of the composition.

Preferably, the composition of the present invention may comprise UV filters able to screen the skin against the action of ultraviolet radiation. Examples of UV filters are, for example, acrylates such as 2-ethylhexyl 2-cyano-3,3-diphenylacrylate (PARSOL 340) and ethyl 2-cyano-3,3-diphenylacrylate, camphor derivatives such as camphor 4-methyl benzylidene (PARSOL 5000), and camphor 3-benzylidene, cinnamates such as octyl methoxycinnamate (PARSOL MCX), ethoxyethyl methoxycinnamate, diethanolamine methoxycinnamate (PARSOL Hydro), triazone derivatives such as ethylhexyl triazone (UVINUL T-150), diethylhexyl butamide triazone (UVASORB HEB), dibenzoylmethane derivatives such as 4-tert-butyl-4'-methoxydibenzoylmethane (PARSOL 1789), dimethoxydibenzoylmethane, benzotriazole derivatives such as 2,2'-methylene-bis(6-(2H-benzotriazol-2-yl)-4-(1,1,3,3-tetramethylbutyl)-phenol (TINOSORB M), triazine derivatives such as bis-ethylhexyloxyphenol methoxyphenyl triazine (TINOSORB S). Other examples of UV filters usable in the topical composition of the present invention may be found in annex VI of the regulation (EC) No. 1223/2009 dated 30 Nov. 2009.

Preferably, the composition of the present invention comprises a total amount of UV filters of from about 0.1% to about 20%, more preferably of from 0.5% to 15% by weight relative to the total weight of the composition.

The following examples will illustrate at least one embodiment of the invention, but without in any way limiting the extent of the protection that is defined in the claims appended hereto.

EXAMPLES

Example 1—Niosomes

A number of formulations of plant extracts embedded in hydrophilic vesicles (niosomes), having the composition given in Table 1 below, were prepared. The resulting composition had the appearance of a uniform, transparent viscous gel. The percentage by weight relative to the total weight of the composition is given for each component.

TABLE 1

| Component | Nio-HMR | Nio-RCL | Nio-GIN | Nio-MRT |
|---|---|---|---|---|
| Soavirol OV6 | 15-25 | 15-25 | 15-25 | 15-25 |
| Nikkol Hexaglyn 1-L | 20-25 | 20-25 | 20-25 | 20-25 |
| Glycerin | 10-20 | 10-20 | 10-20 | 10-20 |
| Magnolol | 0.5-3 | 0.5-3 | 0.5-3 | 0.5-3 |
| Honokiol | 0.5-3 | 0.5-3 | 0.5-3 | 0.5-3 |
| Norway spruce extract (HMR) | 3-5 | — | — | — |
| Red clover extract (RCL) | — | 3-5 | — | — |
| Ginkgo biloba extract (GIN) | — | — | 3-5 | — |
| Bilberry extract (MRT) | — | — | — | 3-5 |
| Water | 30-40 | 30-40 | 30-40 | 30-40 |

Soavirol OV6: Polyglyceryl-6 ester of olive oil
Nikkol Hexaglyn 1-L: Polyglyceryl-6 laurate The extract of Norway spruce, *Picea abies*, containing HMRlignan, was obtained from the knots of the tree subjected to hot extraction with ethanol. The extracted fractions were then co-crystallized with potassium acetate in a ternary system of solvents (ethanol, ethyl acetate and water), until a precipitate was obtained. The precipitate was then filtered and dried to yield the compound in powder form.

Reproducibility of the pharmacological composition of its active substances is obtained by special selection of European *Picea abies* plants, collecting the wood in controlled conditions, and with a standardized extraction and purification process.

The red clover extract was obtained from the leaves, subjected to hot extraction with aqueous ethanol. The extracted fractions were then diluted with water and purified by liquid/liquid extractions. The purified liquid was then concentrated to remove the ethanol and, finally, further concentrated, filtered and dried to obtain the final extract in powder form.

The reproducibility of the pharmacological composition of its active substances is obtained by special cultivation of plants of red clover (grown in Europe), which are grown in controlled conditions, and with a standardized extraction and purification process.

The extract of *Gingko biloba* was obtained from the leaves, subjected to hot extraction with aqueous ethanol. The extracted fractions were then concentrated at reduced pressure to remove the extraction solvent, and purified by filtration on resin-based columns and solid/liquid extractions. The organic solvents were then exchanged with water and finally the aqueous phase was concentrated and dried to obtain the final extract in powder form.

The reproducibility of the pharmacological composition of its active substances is obtained by special cultivation of *Ginkgo biloba* plants (grown in Europe and North America), which are grown in controlled conditions, and with a standardized extraction and purification process.

The bilberry extract was obtained from the fruits, subjected to extraction with ethanol. The extracted fractions were then concentrated at reduced pressure to remove the extraction solvent and purified by filtration on a resin column to remove the sugary components. The organic solvents were then exchanged with water and the aqueous phase was finally lyophilized by a spray-drying technique to obtain the extract in powder form.

The reproducibility of the pharmacological composition of its active substances is obtained by selecting bilberry plants (harvested in Europe), the fruits of which are harvested in controlled conditions, and with a standardized extraction and purification process.

Example 2—Emulsions

A series of emulsions was prepared comprising the formulations of plant extracts embedded in hydrophilic vesicles obtained as described above in example 1.

The composition of the emulsions is given in Table 2 below.

TABLE 2

| Component | Emu-COM | Emu-HMR | Emu-RCL | Emu-GIN | Emu-MRT |
|---|---|---|---|---|---|
| Glyceryl stearate SE | 3.50 | 3.50 | 3.50 | 3.50 | 3.50 |
| Cetearyl alcohol | 4.00 | 4.00 | 4.00 | 4.00 | 4.00 |
| Cyclopentasiloxane | 8.00 | 8.00 | 8.00 | 8.00 | 8.00 |
| Dimethicone | 0.30 | 0.30 | 0.30 | 0.30 | 0.30 |
| Argan oil | 2.00 | 2.00 | 2.00 | 2.00 | 2.00 |
| Tocopheryl acetate | 0.50 | 0.50 | 0.50 | 0.50 | 0.50 |
| Carbomer | 0.25 | 0.25 | 0.25 | 0.25 | 0.25 |
| Propylene glycol | 1.50 | 1.50 | 1.50 | 1.50 | 1.50 |
| Phenoxyethanol & ethylhexylglycerin | 0.80 | 0.80 | 0.80 | 0.80 | 0.80 |
| Perfume (Symrise) | 0.25 | 0.25 | 0.25 | 0.25 | 0.25 |
| Sodium hydroxide (30% sol.) | 0.25 | 0.25 | 0.25 | 0.25 | 0.25 |
| Nio-HMR | — | 2.00 | — | — | — |
| Nio-RCL | — | — | 3.00 | — | — |
| Nio-GIN | — | — | — | 3.00 | — |
| Nio-MRT | — | — | — | — | 3.00 |
| Water sufficient to | 100 | 100 | 100 | 100 | 100 |

Samples of each representative emulsion of the present invention and of the comparative emulsion were submitted to the tests of efficacy described below.

Example 3a—Short-Term Hydration Test

The short-term (one hour) hydrating and protecting efficacy was evaluated as the hydration index measured using a Dermalab Combo with Multi Parameter unit ((Cortex Technology ApS—Hadsund Denmark), with Moisture Pin Probe, which makes it possible to evaluate skin hydration by measuring conductance in microsiemens ($\mu$S) between the stratum corneum and the sensor of the probe of the equipment. The measurement was carried out on a region of the skin of the face as flat as possible, taking care to exert a constant pressure for a time that is predetermined by the instrument itself. The sensor was kept clean each time. The hydration index was measured in conditions of a temperature of about 20° C. and about 40-60% of environmental humidity.

The sample was applied according to its characteristics of use. Its effectiveness was evaluated with a short-term test lasting 1 hour.

The area used for the test is a region of the forehead skin delimited beforehand with surgical tape in which a square cut-out was made, with an area of 6 cm$^2$. Such adhesive tape remained in place throughout the test.

The instrumental evaluations were performed at time t0 (baseline value), and at 5 (t5), 15 (t15), 30 (t30), and 60 (t60) minutes after application of the product.

Before the test, each volunteer was asked not to wash the face, for at least 3 hours preceding the experiment.

Before the test, the subjects remained in the clinic for 30 minutes, to acclimatize the skin to the temperature and humidity of the air-conditioned room in which the tests were performed. At the end of this time, measurement of the baseline values of hydration was carried out.

The test was carried out on 12 subjects of both sexes (6 male, 6 female), aged between 26 and 53 years with an average of 37.4 years. The subjects selected did not have dermatological pathologies or pathologies of some other nature, they were not on any drug treatment, and had not declared intolerance to products for topical use. All the subjects completed the full course of treatment.

The test was carried out firstly with the comparative emulsion (Emu-COM) and with the emulsions comprising the extracts of Norway spruce (Emu-HMR) and of red clover (Emu-RCL).

The results are summarized in Table 3 below, which shows the mean value of the hydration index of the 12 subjects measured at the various observation times for the test emulsion and for the placebo. All the data were submitted to analysis of variance (ANOVA) for repeated measurements followed by the Tukey post-test.

TABLE 3

|  | t0 | t5 | t15 | t30 | t60 |
|---|---|---|---|---|---|
| Emu-COM | 95 | 191 | 177 | 159 | 138 |
| Emu-HMR | 95 | 219** | 206** | 175*** | 151** |
| Emu-RCL | 95 | 214*** | 213* | 178** | 143*** |

*p < 0.01
**p < 0.05
***p > 0.05

Two months later the test was repeated using an identical comparative emulsion (Emu-COM) and the emulsions prepared with the extracts of *ginkgo biloba* (Emu-GIN) and bilberry (Emu-MRT).

The results are summarized in Table 4 below, which gives mean value of the hydration index of the 12 subjects measured at the various observation times for the test emulsion and for the placebo. All the data were submitted to analysis of variance (ANOVA) for repeated measurements followed by the Tukey post-test.

TABLE 4

|  | t0 | t5 | t15 | t30 | t60 |
|---|---|---|---|---|---|
| Emu-COM | 153 | 176 | 158 | 153 | 155 |
| Emu-GIN | 152 | 189*** | 192* | 176** | 157*** |
| Emu-MRT | 149 | 201** | 191° | 176* | 162*** |

°p < 0.001
*p < 0.01
**p < 0.05
***p > 0.05

Example 3b—Long-Term Hydration Test

The method described in example 3b was repeated, asking the same subjects to apply the test product and the placebo twice daily, on waking in the morning and at bedtime, on two different regions of the forehead skin delimited beforehand with surgical tape, in which a square cut-out was made, with an area of 6 cm². The instrumental evaluations were performed at time t0 (baseline value), and at 7 (t7), 14 (t14), and 28 (t28) days.

The results are summarized in Table 5 below, which gives the mean value of the percentage changes in the hydration index of the 12 subjects measured at the various observation times relative to the baseline value for the test emulsion and for the placebo. All the data were analysed using the Student t-test for paired data.

TABLE 5

|  | t0 | t7 | t14 | t28 |
|---|---|---|---|---|
| Emu-COM | 100 | 108 | 107 | 106 |
| Emu-HMR | 100 | 117* | 117* | 115° |
| Emu-RCL | 100 | 113*** | 119* | 121° |
| Emu-GIN | 100 | 111*** | 110* | 112° |
| Emu-MRT | 100 | 108*** | 112* | 116° |

°$p < 0.001$
*$p < 0.01$
**$p < 0.05$
***$p > 0.05$

Example 4—TEWL Long-Term Hydration Test

The long-term (28 days) hydrating and protecting efficacy was evaluated by measuring the transcutaneous water loss (Trans Epidermal Water Loss, TEWL). The TEWL, i.e. the amount of water that migrates from the dermis and from the epidermis through the stratum corneum to the external environment, is a sensitive indicator of the integrity of the skin barrier. Since the TEWL increases with advancing age, this is also taken as a reference parameter for evaluating the anti-ageing efficacy of cosmetics.

For the evaluation a SkinLab Combo instrument (Cortex Technology ApS-Hadsund Denmark), which determines the TEWL by the "Nilsson vapour pressure gradient" open-chamber method, was used, in accordance with the guidelines of the "Standardization Group of European Society of Contact Dermatitis" (Guidelines for transepidermal water loss (TEWL) measurement).

The sample was applied according to its usage characteristics. Its efficacy was evaluated in a long-term test lasting 4 weeks.

The area used for the test is a region of skin of the inner right forearm delimited beforehand with surgical tape, in which a square cut-out was made, with an area of 6 cm². Such adhesive tape remained in place throughout the test.

The instrumental evaluations were performed at time t0 (baseline value), and at 7 (t7d), 14 (t14d), and 28 (t28d) days after application of the product.

Before the test, each volunteer was asked not to wash the region of the forearm involved in the test for at least 3 hours preceding the experiment.

Before the test, the subjects remained in the clinic for 30 minutes, to acclimatize the skin to the temperature and humidity of the air-conditioned room in which the tests were performed. Measurement of the TEWL was undertaken at the end of this time.

The test was carried out on 12 subjects of both sexes (6 male, 6 female), aged between 26 and 53 years with an average age of 37.4 years. The subjects selected did not have dermatological pathologies or pathologies of some other nature, they were not on any drug treatment, and had not declared intolerance to products for topical use. All the subjects completed the full course of treatment.

The results are summarized in Table 6 below, which gives the mean value of the percentage changes in the TEWL of the 12 subjects measured at the various observation times relative to the baseline value for the test emulsion and for the placebo. All the data were submitted to analysis of variance (ANOVA) for repeated measurements followed by the Tukey post-test.

TABLE 6

|  | t0 | t7 | t14 | t28 |
|---|---|---|---|---|
| Emu-COM | 100 | −4.68 | −4.94 | −5.11 |
| Emu-HMR | 100 | −15.64* | −17.03° | −18.50° |
| Emu-RCL | 100 | −13.68* | −14.24* | −13.93** |
| Emu-GIN | 100 | −9.16° | −11.71° | −13.89° |
| Emu-MRT | 100 | −7.84*** | −10.54* | −11.12° |

°$p < 0.001$
*$p < 0.01$
**$p < 0.05$
***$p > 0.05$

Example 5—Long-Term Elasticity Test

The effectiveness on long-term improvement of skin elasticity (28 days) was evaluated using SkinLab Combo equipment with a skin-measuring probe. The measurement of elasticity is based on two separate phases: an aspiration phase applied on the surface of the skin and a release phase. The measuring probe consists of a vacuum chamber with adhesive tape for better adherence to the folds of the skin.

During the aspiration and release phases, the instrument records how the skin rises and then retracts, measuring the three physical parameters that are descriptive of the elasticity of the skin, namely (i) Young's modulus (E), (ii) the skin retraction time R (the time taken for the skin to return from the fully extended situation to the starting situation) and (iii) the skin viscoelasticity (VE), which combines together the data relating to the phase of suction/elevation of the skin with those of release/retraction.

The sample was applied according to its usage characteristics. Its efficacy was evaluated in a long-term test lasting 4 weeks.

The area used for the test is a region of skin of the inner right forearm delimited beforehand with surgical tape, in which a square cut-out was made, with an area of 6 cm². Such adhesive tape remained in place throughout the test.

The instrumental evaluations were performed at time t0 (baseline value), and at 7 (t7d), 14 (t14d), and 28 (t28d) days after application of the product.

Before the test, each volunteer was asked not to wash the region of the forearm involved in the test for at least 3 hours preceding the experiment.

Before the test, the subjects remained in the clinic for 30 minutes, to acclimatize the skin to the temperature and humidity of the air-conditioned room in which the tests were performed. At the end of this time, measurements were taken of Young's modulus (E), the skin retraction time (R), and the skin viscoelasticity (VE).

The test was carried out on 12 subjects of both sexes (6 male, 6 female), aged between 26 and 53 years with an average age of 37.4 years. The subjects selected did not have dermatological pathologies or pathologies of some other nature, they were not on any drug treatment, and had not declared intolerance to products for topical use. All the subjects completed the full course of treatment.

The results are summarized in Tables 7-9 below, which give the mean values of the percentage changes in E, R and VE of the 12 subjects measured at the various observation times relative to the baseline value for the test emulsion and for the placebo. All the data were submitted to analysis of variance (ANOVA) for repeated measurements followed by the Tukey post-test.

TABLE 7

Young's modulus (E)

|  | t0 | t7 | t14 | t28 |
|---|---|---|---|---|
| Emu-COM | 100 | −5.58 | −6.16 | −6.25 |
| Emu-HMR | 100 | −9.55*** | −12.64* | −13.98* |
| Emu-RCL | 100 | −12.55** | −15.11* | −17.14* |
| Emu-GIN | 100 | −13.80** | −15.07* | −16.78* |
| Emu-MRT | 100 | −14.48** | −17.02* | −17.28* |

°$p < 0.001$
*$p < 0.01$
**$p < 0.05$
***$p > 0.05$

TABLE 8

Skin retraction time (R)

|  | t0 | t7 | t14 | t28 |
|---|---|---|---|---|
| Emu-COM | 100 | −5.81 | −6.50 | −6.52 |
| Emu-HMR | 100 | −10.05*** | −15.54* | −16.68* |
| Emu-RCL | 100 | −13.43** | −16.47* | −19.02* |
| Emu-GIN | 100 | −12.54** | −15.92* | −17.77* |
| Emu-MRT | 100 | −12.79** | −16.85* | −18.22* |

°$p < 0.001$
*$p < 0.01$
**$p < 0.05$
***$p > 0.05$

TABLE 9

Viscoelasticity (VE) of the skin

|  | t0 | t7 | t14 | t28 |
|---|---|---|---|---|
| Emu-COM | 100 | −4.82 | −5.58 | −5.79 |
| Emu-HMR | 100 | −8.45*** | −11.48* | −13.88* |
| Emu-RCL | 100 | −11.93** | −14.36* | −16.28* |
| Emu-GIN | 100 | −11.14** | −13.61* | −15.15* |
| Emu-MRT | 100 | −10.65** | −13.42* | −15.24* |

°$p < 0.001$
*$p < 0.01$
**$p < 0.05$
***$p > 0.05$

Example 6—Long-Term Test of Anti-Ageing Effect

The effectiveness of the test product in producing a long-term increase in skin thickness and dermal density (56 days) was evaluated using SkinLab Combo equipment with a high-frequency ultrasound probe (20 MHz).

Analysis of the high-resolution image obtained using high-frequency ultrasound (20 MHz) allows in-vivo investigation of physiological and pathological processes occurring in the skin. The methodology is based on measurement of the acoustic response obtained when a high-frequency sound pulse is propagated within the skin. For all practical purposes, when this impinges on the various structures of the skin, part of the pulse is reflected and part is transmitted further. The reflected signal is collected by an ultrasound transducer and, after processing, is converted into an image of the cross-section of skin on which the sound waves impinge. Such image has different degrees of luminous intensity as a function of the intensity of the acoustic signals reflected in a colour scale, where dark colours represent regions of skin with low reflection (i.e. no change or small changes in density between the cutaneous structures), and bright colours (from green to white, via yellow and red) represent the regions that are able to generate reflected signals of high intensity owing to significant changes in structural density.

Changes in the extracellular matrix that occur during the skin ageing process, can be quantified in terms of changes in skin thickness, dermal density and echogenicity. The latter is determined as pixels of different colours: white-yellow-red-green-blue-black. In an image of healthy skin, the epidermal echogenicity appears as a white band, and conversely the dermis appears heterogeneously coloured with coloured pixels ranging from red/yellow to green, and the hypodermis appears black.

The sample was applied according to its usage characteristics. Its efficacy was evaluated in a long-term test lasting 8 weeks.

The area used for the test is a region of skin of the inner right forearm delimited beforehand with surgical tape, in which a square cut-out was made, with an area of 6 cm$^2$. Such adhesive tape remained in place throughout the test.

The instrumental evaluations were performed at time t0 (baseline value), and at 28 (t28) and 56 (t56) days after application of the product.

Before the test, each volunteer was asked not to wash the region of the forearm involved in the test for at least 3 hours preceding the experiment.

Before the test, the subjects remained in the clinic for 30 minutes, to acclimatize the skin to the temperature and humidity of the air-conditioned room in which the tests were performed. Ultrasonography measurement was carried out at the end of this time.

The test was carried out on 12 subjects of both sexes (6 male, 6 female), aged between 26 and 53 years with an average age of 37.4 years. The subjects selected did not have dermatological pathologies or pathologies of some other nature, they were not on any drug treatment, and had not declared intolerance to products for topical use. All the subjects completed the full course of treatment.

The results are summarized in Tables 10 and 11 below, which give the mean values of skin thickness (in mm) and dermal density (in pixel intensity) of the 12 subjects measured at the various observation times for the test emulsion and for the placebo. All the data were submitted to analysis of variance (ANOVA) for repeated measurements followed by the Tukey post-test.

TABLE 10

Skin thickness

|  | t0 | t28 | t56 |
|---|---|---|---|
| Emu-COM | 1.365 | 1.362 | 1.376 |
| Emu-HMR | 1.385 | 1.452° | 1.501° |
| Emu-RCL | 1.387 | 1.419* | 1.470° |

TABLE 10-continued

Skin thickness

|         | t0    | t28      | t56     |
|---------|-------|----------|---------|
| Emu-GIN | 1.376 | 1.403*   | 1.413°  |
| Emu-MRT | 1.392 | 1.391*** | 1.401***|

°p < 0.001
*p < 0.01
**p < 0.05
***p > 0.05

TABLE 11

Dermal density

|         | t0    | t28      | t56      |
|---------|-------|----------|----------|
| Emu-COM | 52.00 | 52.17    | 52.89    |
| Emu-HMR | 49.50 | 60.39°   | 65.28°   |
| Emu-RCL | 51.72 | 59.72**  | 64.33°   |
| Emu-GIN | 50.69 | 55.25*** | 59.94**  |
| Emu-MRT | 51.69 | 53.25*** | 56.06*** |

°p < 0.001
*p < 0.01
**p < 0.05
***p > 0.05

Example 7—Test of Antimicrobial Resistance (Challenge Test)

The test consists of "challenging" the preparation with a defined inoculum of suitable microorganisms, leaving the inoculated preparation at a stipulated temperature, and withdrawing samples from the container at specific time intervals and counting the number of organisms present in the samples collected.

The test was conducted following the recommendations given in the Italian Pharmacopoeia—Edition IX and using bacterial cultures of the following strains of microorganisms.

| Pseudomonas aeruginosa | ATCC 9027  |
| Escherichia coli       | ATCC 8739  |
| Staphylococcus aureus  | ATCC 6538  |
| Candida albicans       | ATCC 10231 |
| Aspergillus niger      | ATCC 16404 |

Each niosomal formulation containing the plant extracts prepared as described in example 1 was inoculated with the various microorganisms with an inoculum comprising a number of bacteria between $10^5$ and $10^6$ and a number of fungi or moulds between $10^4$ and $10^5$. The inoculated product was stored at room temperature (20-25° C.) away from the light. A sample of product was taken at time t0 (baseline value) and at 2 (t2), 7 (t7), 14 (t14), and 28 (t28) days, for determining the number of microorganisms present.

The results are summarized in Tables 12-16 below, which give the values found, expressed on a logarithmic base, for each product and for each microorganism at the various observation times.

TABLE 12

Escherichia coli

|         | t0   | t2   | t7 | t14 | t28 |
|---------|------|------|----|-----|-----|
| Nio-HMR | 5.69 | 1.47 | <1 | <1  | <1  |
| Nio-RCL | 5.69 | 1.60 | <1 | <1  | <1  |
| Nio-GIN | 5.69 | 1.47 | <1 | <1  | <1  |
| Nio-MRT | 5.69 | 1.00 | <1 | <1  | <1  |

TABLE 13

Pseudomonas aeruginosa

|         | t0   | t2   | t7 | t14 | t28 |
|---------|------|------|----|-----|-----|
| Nio-HMR | 5.69 | 1.00 | <1 | <1  | <1  |
| Nio-RCL | 5.69 | 1.47 | <1 | <1  | <1  |
| Nio-GIN | 5.69 | 1.00 | <1 | <1  | <1  |
| Nio-MRT | 5.69 | 1.00 | <1 | <1  | <1  |

TABLE 14

Staphylococcus aureus

|         | t0   | t2   | t7 | t14 | t28 |
|---------|------|------|----|-----|-----|
| Nio-HMR | 5.69 | 1.00 | <1 | <1  | <1  |
| Nio-RCL | 5.69 | 1.00 | <1 | <1  | <1  |
| Nio-GIN | 5.69 | 1.47 | <1 | <1  | <1  |
| Nio-MRT | 5.69 | 1.30 | <1 | <1  | <1  |

TABLE 15

Candida albicans

|         | t0   | t2 | t7 | t14 | t28 |
|---------|------|----|----|-----|-----|
| Nio-HMR | 4.69 | <1 | <1 | <1  | <1  |
| Nio-RCL | 4.69 | <1 | <1 | <1  | <1  |
| Nio-GIN | 4.69 | <1 | <1 | <1  | <1  |
| Nio-MRT | 4.69 | <1 | <1 | <1  | <1  |

TABLE 16

Aspergillus niger

|         | t0   | t2 | t7   | t14 | t28 |
|---------|------|----|------|-----|-----|
| Nio-HMR | 4.69 | 3  | <1   | <1  | <1  |
| Nio-RCL | 4.69 | 3  | 1.78 | <1  | <1  |
| Nio-GIN | 4.69 | 3  | <1   | <1  | <1  |
| Nio-MRT | 4.69 | 3  | <1   | <1  | <1  |

On the basis of the results obtained, all the niosomal formulations under investigation passed the challenge test, displaying inhibitory activity against all the microorganisms according to the acceptability criteria laid down by the CTPA (Cosmetic, Toiletry, and Perfumery Association) and the CTFA (Cosmetic, Toiletry, and Fragrance Association), which envisage a reduction equal to 99.9% of the bacteria and 90% of the moulds or fungi inoculated, within 7 days from inoculation, and a further reduction subsequently.

Example 8—Test of the Soothing Effect of the Niosomes of Plant Extracts of Norway Spruce The effectiveness of the niosome prepared with extract of Norway spruce (Nio-HMR), formulated as emulsion (Emu- HMR), in determining a reduction of skin sensitization was determined using the SkinLab Combo equipment (Cortex Technology Denmark) equipped with a colorimetric probe. The SkinLab colorimetric probe, thanks to the "Erythema" function, is able to measure specifically the haemoglobin content in the skin, thus providing a precise quantification of the value of the erythema index (EI). The higher this value, the greater is the degree of irritation.

For the purpose of inducing an erythematous reaction, the inner region of skin of the forearm was pre-treated with a solution containing sodium lauryl sulphate (SLS) at 5% in occlusion with the aid of Finn chambers (small aluminium cells with a volume of 20 microliters) for about 12 hours. At the end of this treatment the occlusive plasters containing the small aluminium cells were removed. After a time interval of 12 hours, an amount of sample equal to 2.0 mg/cm$^2$ was applied on the areas of irritated skin.

The test was carried out with the product Emu-HMR, having the product Emu-COM as comparison, with a commercially available anti-inflammatory cream based on hydrocortisone-17-butyrate at 0.1% as positive control (C+), and distilled water as negative control (C—). For each subject, each product was applied on a different region of the previously sensitized forearm.

The test was carried out on 12 subjects of both sexes (6 male, 6 female), aged between 26 and 53 years with an average age of 37.4 years. The subjects selected did not have dermatological pathologies or pathologies of some other nature, they were not on any drug treatment, and had not declared intolerance to products for topical use. All the subjects completed the full course of treatment.

Throughout the test, the subjects were instructed (i) not to apply products and/or detergents on the region involved in the treatment, (ii) not to get the plaster wet, (iii) not to engage in sports activities, and (iv) to avoid exposure to UVA and UVB radiation.

The instrumental evaluations were performed at time t0 (baseline value), and at 30 (t30), 60 (t60) and 120 (t120) minutes after application of the product.

The results are summarized in Table 17 below, which gives the mean values of the erythema index (EI) of the 12 subjects measured at the various observation times in the areas treated with the test product, the placebo, and the positive and negative control. All the data were submitted to analysis of variance (ANOVA) for repeated measurements followed by the Tukey post-test.

TABLE 17

| Erythema index (EI) | | | | |
|---|---|---|---|---|
| | t0 | t30* | t60* | t120* |
| Emu-HMR | 33.08 | 31.25 | 25.00 | 21.50 |
| Emu-COM | 31.83 | 32.83 | 31.67 | 30.17 |
| Cream C+ | 33.92 | 27.42 | 24.17 | 19.92 |
| Water C– | 31.75 | 32.92 | 33.33 | 32.33 |

*$p \leq 0.0001$

Example 9—Skin Absorption Test (Permeation Test)

The test consists of evaluating the kinetics of diffusion of the active principles contained in the niosomal formulation for topical use, after various contact times of the aforementioned niosomal formulation with a synthetic membrane model, simulating, as far as is compatible with the model, the conditions of use in vivo. The active principles of the niosomal formulation optionally released and able to cross the epidermal barrier are sought, at various treatment times, in the receiving section of the Franz cell and quantified by HPLC-DAD.

The test for evaluating transmembrane diffusion was conducted using the Franz cell model according to the method described in USP 1724 (2015) SemiSolid Drug Products and using Strat-M® membranes (EMD Millipore). The Strat-M® membranes are synthetic membranes used for transmembrane diffusion tests, which simulate the diffusion of various types of compounds and formulations in the human epidermis.

The test was performed for the active principles biochanin A (CAS No.: 491-80-5) and formononetin [CAS No.: 485-72-3] contained in the niosomal formulation with red clover extract, 7-HMR (7-hydroxymatairesinol) contained in the niosomal formulation with extract of Norway spruce, quercetin contained in the niosomal formulation with *ginkgo biloba*, and anthocyanins contained in the niosomal formulation with bilberry.

Each niosomal formulation containing the plant extracts prepared as described in example 1 was applied on the membranes (1 g/cm$^2$) by means of the P100 Gilson special positive-displacement pipette for dense liquids. By weighing the Franz cell using an analytical balance before and after application, it was possible to measure out the sample accurately. The niosomal formulations were applied as such on the Strat-M® membrane. The extracts as such were suspended at 3% in glycerin and then applied on the Strat-M® membrane. This way, the comparison between the active ingredients in the samples was adequately carried out.

The negative control is represented by membranes treated with phosphate buffer.

The samples and the controls were incubated at 32° C., 5% $CO_2$ and they were exposed for 3 and/or 6 and/or 24 and/or 48 hours. Each sample was tested in triplicate. At the various exposure times, samples were taken of part of the receiving liquid with a syringe.

The samples thus collected were immediately put in the refrigerator at +4° C. and were then taken for quantitative chromatographic analyses. At the end of exposure, the integrity of the epidermal barrier was evaluated with fluorescein.

The results are summarized in Tables 18-20 below, which give the values found for each product at the various observation times.

TABLE 18

| | | Average diffusion (μg/cm$^2$) | |
|---|---|---|---|
| | | T1 (6 hours) | T2 (24 hours) |
| RCL 3% glycerin | Biochanin A | <0.50 | 2.02 (0.84)* |
| | Formononetin | <0.50 | 1.11 (0.54)* |
| Nio-RCL | Biochanin A | <0.50 | 10.68 (1.67)* |
| | Formononetin | <0.50 | 15.48 (2.03)* |

*p value < 0.05

The transmembrane diffusion analysed in vitro on the STRAT M® membrane, of biochanin A and formononetin within the products (RCL 3% glycerin and Nio-RCL) showed diffusion below analytical detectability limit (<0.50 μg/cm$^2$) at time T1 for both active ingredients of both products.

In contrast, at time T2 the transmembrane diffusion of the two active principles is detectable for both products, but the quantity diffused in the niosomal formulation (Nio-RCL) is significantly greater for both active principles with respect to the quantity diffused from the sample of red clover extract suspended in glycerin (RCL 3% glycerin).

TABLE 19

|  |  | Average diffusion ($\mu g/cm^2$) | |
|---|---|---|---|
|  |  | T1 (3 hours) | T2 (6 hours) |
| HMRlignan 2% glycerin | 7-HMR | <0.25 | 0.66 (0.38)* |
| Nio-HMR | 7-HMR | 23.5 (6.50) | 96.90 (20.2)* |

*p value < 0.05

The transmembrane diffusion analysed in vitro on the STRAT M® membrane, of 7-hydroxymatairesinol (7-HMR) within the products (HMRlignan 2% glycerin and Nio-HMR) showed very different behaviours of the two products already at time T1.

After 3 hours, the sample of extract of HMRlignan suspended in glycerin (HMRlignan 2% glycerin) showed diffusion below the analytical detectability limit (<0.25 $\mu g/cm^2$), while the diffusion of the niosomal formulation (Nio-HMR) was well above the detectability threshold, quantifiable as 23.5 $\mu g/cm^2$.

At time T2, the transmembrane diffusion of the two active principles is detectable for both products, but the quantity diffused in the niosomal formulation (Nio-HMR) is significantly greater with respect to the quantity diffused from the sample HMRlignan 2% glycerin, which remains rather low (0.66 $\mu g/cm^2$).

TABLE 20

|  |  | Average diffusion ($\mu g/cm^2$) | | | |
|---|---|---|---|---|---|
|  |  | T1 (3 hours) | T2 (6 hours) | T3 (24 hours) | T4 (48 hours) |
| GIN 3% glycerin | Quercetin | <0.40 | <0.40 | <0.40 | 7.1 (7.9)* |
| Nio-GIN | Quercetin | <0.40 | <0.40 | 4.9 (3.8)* | 12.4 (0.4)* |

*p value < 0.05

The transmembrane diffusion analysed in vitro on the STRAT M® membrane, of quercetin within the product GIN 3% glycerin showed, up to 24 hours, diffusion that is below the analytical detectability limit (<0.40 $\mu g/cm^2$; times T1, T2 and T3), and only detectable after 48 hours (time T4), quantifiable as 7.1 $\mu g/cm^2$.

Advantageously, the niosomal formulation (Nio-GIN) showed diffusion below the analytical detectability limit (<0.40 $\mu g/cm^2$), only up to 6 hours (times T1 and T2), whereas it was detectable after 24 hours (time T3), quantifiable as 4.9 $\mu g/cm^2$, and after 48 hours (time T4), quantifiable as 12.4 $\mu g/cm^2$.

Advantageously, although at time T4 the transmembrane diffusion of the two active principles is detectable for both products, the quantity diffused in the niosomal formulation (Nio-GIN) is significantly greater with respect to the quantity diffused from the sample of *ginkgo biloba* extract suspended in glycerin (GIN 2% glycerin).

Substantially similar results were obtained for the niosomal compositions containing bilberry extract (Nio-MRT).

Example 10—Toxicity Test

The safety of use of the niosomal formulations prepared as described in example 1 was verified by in-vitro assays for evaluating the irritant power at the level of the skin and mucosae, both in general and in particular in the ocular compartment, by determining the cytotoxicity measured with the MTT assay (3-(4,5-dimethylthiazol-2-yl)-2,5-diphenyltetrazolium bromide).

This assay measures the activity of the mitochondrial enzyme succinate dehydrogenase, which is only active in living cells and reacts with MTT (coloured yellow) forming a blue coloured salt, whose optical density ($OD_n$), which is proportional to the number of live cells, is quantified spectrophotometrically at a wavelength of 570 nm.

Tests were carried out on a model of reconstituted human epidermis and on a model of reconstructed human corneal epithelium.

The in-vitro protocol based on the use of reconstituted human epidermis was validated by EVCAM (http://ecvam.jrc.ec.europa.eu) and accepted by the OECD/OCSE 439 guidelines as an alternative model to the use of animals, and is described hereunder.

The tissues, after incubation in culture medium (EPI-100-NMM), were treated with 25 mg of niosomal formulation. The positive control (PC) was prepared by treating the tissues with 30 μL of a 5% solution of SDS (sodium lauryl sulphate), and the negative control (CN) by treating the tissues with 30 μL of DPBS (Dulbecco's Phosphate Buffered Saline, Euroclone).

After treatment, the tissues were incubated for 60 minutes (37° C., 5% $CO_2$), washed with phosphate buffer and incubated again in clean culture medium for 24 hours (37° C., 5% $CO_2$), they were then transferred again into fresh culture medium and incubated for a further 18 hours (37° C., 5% $CO_2$).

Next, the tissues were transferred to a 1 mg/mL solution of MTT in DPBS and incubated for 3 hours (37° C., 5% $CO_2$), then transferred to isopropanol and incubated for 2 hours in the dark at room temperature.

At the end of the process, spectrophotometric reading was performed at a wavelength $\lambda=570$ nm using the Microplate Spectrophotometer μQUANT BIO TEK-US. The values of optical density obtained for the treated samples and for the controls were normalized with respect to the values obtained for isopropanol alone.

The results are summarized in Table 21 below, which gives the mean values of $OD_n$ (n=6, 2 aliquots, 3 tissue samples) and of percentage cellular vitality obtained for the tissues treated with each niosomal formulation and for the associated positive and negative controls.

The degree of cellular vitality was calculated from the following formula:

% cellular vitality=[$OD_n$(570 nm) compound tested/$OD_n$(570 nm) negative control]×100

A compound must be classified as irritant (R38) if the cellular vitality is found to be less than or equal to 50%, whereas it can be classified as non-irritant when this exceeds 50%.

TABLE 21

| Evaluation of the irritant power in vitro on a model of reconstituted human epidermis | | |
|---|---|---|
|  | Mean $OD_n$ | Mean cellular vitality (%) |
| Negative Control | 1.41 ± 0.30 | 100.3 ± 19 |
| Positive Control | 0.03 ± 0.02 | 2.12 ± 1.2 |
| Nio-RCL | 1.42 ± 0.17 | 100.4 ± 11.8 |
| Nio-HMR | 1.35 ± 0.2 | 95.6 ± 16.9 |
| Nio-GIN | 1.28 ± 0.12 | 90.8 ± 8.7 |
| Nio-MRT | 0.87 ± 0.12 | 61.4 ± 8.9 |

It can be concluded from the results obtained in the test for evaluating irritant power in vitro, on reconstituted human epidermis, that all the niosomal formulations of the present invention can be classified as non-irritant (cellular vitality>50%).

The in-vitro protocol based on the use of a model of reconstructed human corneal epithelium is validated by EVCAM (http://ecvam.jrc.ec.europa.eu) and accepted by the OECD TG492 guidelines as an alternative model to the use of animals, and is described hereunder.

The tissues, after incubation in culture medium based on DMEM (Dulbecco's Modified Eagle's medium; OCL-200-ASY), were treated with 20 µL of DPBS and incubated for 30 minutes (37° C., 5% $CO_2$). Next, 50 µL of niosomal formulation were added. The positive control (PC) was produced by adding 50 µL of methyl acetate to the tissues, and the negative control (CN) by adding 50 µL of sterile deionized water.

After treatment, the tissues were incubated for 30 minutes (37° C., 5% $CO_2$), subjected to washing with DPBS and incubated again in clean culture medium for 12 minutes (37° C., 5% $CO_2$), then they were transferred to a new hot culture medium and incubated for a further 2 hours (37° C., 5% $CO_2$).

Next, the tissues were transferred to a 1 mg/mL solution of MTT in DPBS and incubated for 3 hours (37° C., 5% $CO_2$), then transferred to isopropanol and incubated overnight in the dark at a temperature of 2-8° C. without shaking.

At the end of the process, spectrophotometric reading was performed at a wavelength $\lambda$=570 nm using the Microplate Spectrophotometer µQUANT BIO TEK-US. The values of optical density obtained for the treated samples and for the controls were normalized with respect to the values obtained for isopropanol alone.

The results are summarized in Table 22 below, which gives the mean values of $OD_n$ (n=12, 4 aliquots, 3 tissue samples) and of percentage cellular vitality obtained for the tissues treated with each niosomal formulation and for the positive and negative controls.

In the case of the test for ocular irritation, a compound must be classified as irritant (R38) if the cellular vitality is found to be less than or equal to 60%, whereas it can be classified as non-irritant when this exceeds 60%.

TABLE 22

Evaluation of the irritant power in vitro on a model of reconstructed human corneal epithelium

| | Mean $OD_n$ | Mean cellular vitality (%) |
|---|---|---|
| Negative Control | 1.13 | 100.0 ± 2.5 |
| Positive Control | 0.39 | 35.09 ± 1.4 |
| Nio-RCL | 0.96 | 84.4 ± 1.6 |
| Nio-HMR | 0.97 | 85.9 ± 3.8 |
| Nio-GIN | 0.88 | 77.8 ± 1.5 |
| Nio-MRT | 1.10 | 96.8 ± 3.3 |

It can be concluded from the results obtained in the test for evaluating irritant power in vitro, on a model of reconstructed human corneal epithelium, that all the niosomal formulations of the present invention can be classified as non-irritant (cellular vitality>60%).

Example 11—Test of Long-Term Effect Against Skin Blotches

The effectiveness of the niosome prepared with red clover extract (Nio-RCL), formulated as an emulsion (Emu-RCL), in determining a reduction in the number of skin blotches and an improvement in the smoothness of the facial skin was evaluated using VISIA II equipment (Canfield Scientific, Inc.).

VISIA II (Canfield Scientific, Inc.) is an image analyser specifically optimized for studying morphological changes of the facial skin. By high-definition photographic scanning, VISIA II is able to acquire, also with the aid of special UV filters, polarized light and fluorescence, detailed morphological information about the condition of the facial skin of the subject undergoing analysis. By means of a multispectral image analyser, VISIA is able to process the photographic information obtained, supplying qualitative and quantitative data regarding eight characteristics that relate to the health and appearance of the skin, such as: (i) pigmentation of the skin, (ii) size and (iii) number of pores, (iv) presence of porphyrins due to bacterial activity (test for bacteria), (v) photo-induced skin blotches, (vi) reddening of the skin, (vii) number and (viii) intensity of wrinkles.

The sample was applied according to its usage characteristics. Its efficacy was evaluated in a long-term test lasting 4 weeks.

The area used for the test with the emulsion of niosome of red clover (Emu-RCL) is the left half of the face. The right half was treated with the comparative emulsion (Emu-COM).

The instrumental evaluations were performed at time T0 (baseline value), and at 7 (T7), and 28 (T28) days after application of the product.

Before the test, each volunteer was asked not to apply face decorative products and not to wash the face, for at least 3 hours preceding the experiment.

Alignment of the camera of the VISIA and balancing of the "White" were carried out before each measurement session.

The test was carried out on 15 subjects of both sexes (6 male, 9 female), aged between 22 and 56 years with an average age of 36.7 years. The subjects selected did not have dermatological pathologies or pathologies of some other nature, they were not on any drug treatment, and showed a type II-IV phenotype (Fitzpatrick). All the subjects completed the full course of treatment.

The results are summarized in Tables 23-25 below, which give the mean values of the percentage changes relative to the baseline value (T0) of the score-spot (qualitative evaluation of blotches), of the number of blotches and of the score-texture (smoothness of the skin) of the 15 subjects, measured at the various observation times for the emulsion under examination (Emu-RCL) and for the comparative emulsion (Emu-COM). All the data were submitted to analysis of variance (ANOVA) for repeated measurements followed by the Tukey post-test.

TABLE 23

Percentage change of score-spot

| | 7 days (%) | 28 days (%) |
|---|---|---|
| Emu-RCL | −1.45 ± 7.7 | −4.21 ± 7.9 |
| Emu-COM | −0.44 ± 3.6 | −2.33 ± 5.5 |

TABLE 24

Percentage change, number of blotches

| | 7 days (%) | 28 days (%) |
|---|---|---|
| Emu-RCL | −3.84 ± 5.2 | −8.99 ± 9.4 |
| Emu-COM | −1.41 ± 3.8 | −3.77 ± 4.3 |

TABLE 25

Percentage change, score-texture

|  | 7 days (%) | 28 days (%) |
|---|---|---|
| Emu-RCL | −14.73 ± 8.0 | −22.12 ± 9.6 |
| Emu-COM | −1.37 ± 3.1 | −4.0 ± 1.9 | p value < 0.001

The emulsion containing Nio-RCL has showed to be significantly effective, with respect to the comparative emulsion, in improving the smoothness of the facial skin and the general texture of the face. Treatment with Emu-RCL also seems to produce a reduction in the number of blotches, not correlated with a reduction in melasma and old-age freckles, as demonstrated by analysis with polarized light, but rather with an improvement in post-inflammatory dyschromia and hyperchromia.

Example 12—Test of Long-Term Anti-Wrinkle Effect

The effectiveness of the niosome prepared with red clover extract (Nio-RCL), formulated as an emulsion (Emu-RCL), for producing a reduction in the number of facial wrinkles and the extent of wrinkles of the under-eye was evaluated using the VISIA II equipment (Canfield Scientific, Inc.) described in example 11.

Its efficacy was evaluated in a long-term test lasting 4 weeks.

The area used for the test is the left half of the face (Emu-RCL). The right half of the face was treated with the comparative emulsion (Emu-COM).

The instrumental evaluations were performed at time T0 (baseline value), and at 7 (T7), 14 (T14), 21 (T21) and 28 (T28) days after application of the product.

Before the test, each volunteer was asked not to apply face decorative products and not to wash the face, for at least 3 hours preceding the experiment.

Alignment of the camera of the VISIA and balancing of the "White" were carried out before each measurement session.

The test was carried out on 15 subjects of both sexes (6 male, 9 female), aged between 26 and 56 years with an average age of 36.7 years. The subjects selected did not have dermatological pathologies or pathologies of some other nature, they were not on any drug treatment, and showed a type II-IV phenotype (Fitzpatrick). All the subjects completed the full course of treatment.

The results are summarized in Tables 26 and 27 below, which give the mean values of the percentage changes relative to the baseline value (t0) of the score-wrinkles (qualitative evaluation of wrinkles), and the number of wrinkles of the 15 subjects, measured at the various observation times for the emulsion under investigation and for the comparative emulsion. All the data were submitted to analysis of variance (ANOVA) for repeated measurements followed by the Tukey post-test.

TABLE 26

Percentage change, score-wrinkles

|  | 7 days (%) | 14 days (%) | 21 days (%) | 28 days (%) |
|---|---|---|---|---|
| Emu-RCL | −26.22 ± 15.9 | −49.38 ± 32.4 | −55.09 ± 29.8 | −59.07 ± 41.4 |
| Emu-COM | −5.57 ± 7.5 | −6.11 ± 7.8 | −14.35 ± 9.1 | −14.30 ± 4.9 | p value < 0.001

TABLE 27

Percentage change, number of wrinkles

|  | 7 days (%) | 14 days (%) | 21 days (%) | 28 days (%) |
|---|---|---|---|---|
| Emu-RCL | −3.5 ± 8.8 | −17.2 ± 18.8 | −19.4 ± 19.8 | −22.3 ± 19.7 |
| Emu-COM | −0.32 ± 8.5 | −2.11 ± 5.8 | −0.97 ± 2.0 | −3.62 ± 7.0 |

The results of the analysis of the skin relief highlighted a significant reduction both in the number and in the total volume of wrinkles present in the measurement grid of the VISIA in the subjects treated with Emu-RCL, with respect to those treated with the comparative emulsion. In particular, a 59% reduction was observed in the total volume of wrinkles and a 22% reduction in the number of wrinkles.

Example 13—Test of Activity on the Microcirculation and Anti-Hair Loss Effect The effectiveness of the niosome prepared with ginkgo extract (Nio-GIN), formulated as an emulsion (Emu-GIN), in reducing and/or stopping hair loss was evaluated by studying the activity and average vitality measured with the MTT assay (3-(4,5-dimethylthiazol-2-yl)-2,5-diphenyltetrazolium bromide), as described in example 10.

A double-blind test was conducted on 40 subjects of both sexes affected by telogen effluvium of grade 2 and 3 (according to the Hamilton-Norwood Scale), aged between 18 and 65 years.

The efficacy was evaluated in a long-term test lasting 3 months.

The area used for the test is the left half of the cranium, treated with the product under investigation (Emu-GIN). The right half was treated with the comparative emulsion (Emu-COM).

The evaluations were performed at time T0 (baseline value), and at 30 (T30), 60 (T60), and 90 (T90) days after application of the product.

The study was divided into the following phases:
1. objective clinical evaluation;
2. trichographic analysis performed with techniques of cellular biology: microtrichographic images of the fronto-vertical area with an LED microcamera, and subsequent evaluation of the biological activity of hair collected from each subject, with evaluation of the average vitality by means of the MTT assay;
3. subjective evaluation by study participants by means of a questionnaire with questions suitable for investigating the perception of effectiveness of the treatment and likeability of the product.

All the data were submitted to analysis of variance (ANOVA) for repeated measurements followed by the Tukey post-test.

The emulsion containing Nio-GIN was found to be significantly effective, relative to the comparative emulsion, in improving the objective and subjective evaluation of the hair. Moreover, trichographic analysis showed an improvement of cellular vitality in the hair collected.

Example 14—Test of Long-Term Effect Against Dark Rings and Bags Under the Eyes

The effectiveness of the niosome prepared with bilberry extract (Nio-MRT), formulated as an emulsion (Emu-MRT), in decongestion and reduction of the volume of subcutaneous bags, and in masking and reducing dark rings, was evaluated by objective and instrumental clinical evaluation.

Reduction of subcutaneous bags was analysed by the Visio-3D DermaTOP Blue technique (Eotech, SA), which allows precise measurement of the same area of skin at the different times of analysis, coupled to the OptoCAT software, used for acquisition, visualization and analysis of the results.

This program is able to supply data on the parameters relating to superficial histo-morphological changes, quantifying the volumes of the reliefs and their variation in an area of 80×75 mm.

The reduction of dark rings was quantified by reflection colorimetry using a Chroma Meter CR-200 (Minolta), and utilizing the components of reflection L*a*b (also known by the name CIELab).

CIELab is a colour-opponent space, based on the coordinates of the compressed non-linear colour space CIE XYZ, in which a colour is identified by three values: the luminance L, expressed as a percentage (0 for black and 100 for white), and the colour-opponent dimensions a and b, colour ranges respectively from green to red and from blue to yellow with values from −120 to +120.

The single-blind study was conducted on 20 subjects aged between 25 and 65 years who showed subcutaneous bags and/or dark rings.

The emulsion with niosome of bilberry extract (Emu-MRT) was applied twice daily, morning and evening. Its efficacy was evaluated in a long-term test lasting 30 days.

The area used for the test is the left peri-ocular region of the face and it was treated with emulsion of niosome of bilberry extract (Emu-MRT). The right one was treated with the comparative emulsion (Emu-COM).

The evaluations were performed at time T0 (baseline value), and at 15 (T15) and 30 (T30) days after application of the product.

The study was divided into the following phases:
1. objective clinical evaluation of the effectiveness of reduction of dark rings and subcutaneous bags;
2. instrumental evaluation of the reduction of subcutaneous bags;
3. instrumental evaluation of the reduction of dark rings.

All the data were submitted to analysis of variance (ANOVA) for repeated measurements followed by the Tukey post-test.

The emulsion containing Nio-MRT was found to be significantly effective, with respect to the comparative emulsion, in the decongestion and reduction of the volume of subcutaneous bags, and in masking and reducing dark rings.

Example 15—Test of Effect Against Dryness of the Mucosae

The effectiveness of the niosome prepared with red clover extract (Emu-RCL), formulated as an emulsion, in providing a reduction of dryness of the vaginal mucosae, was evaluated in an observational clinical study on 40 subjects and was evaluated with a long-term test lasting 90 days (T90).

The parameters considered as indicators of improvement of the vaginal mucosae condition were:
Vulvovaginal burning and dryness evaluated using a visual analogue scale (VAS—scale graded from 0=absence of pain to 10=maximum pain, with indication of the intermediate values according to a rate equal to 0.5).
Dyspareunia evaluated by means of a Marinoff scale (0=No pain; 1=Pain with discomfort, without interference with frequency of intercourse; 2=Pain with interference with frequency of intercourse; 3=Pain prevents intercourse). (Marinoff S C, Turner M L C. Vulvar vestibulitis syndrome. Dermatol Clin 1992; 10:435-44).

The analyses of effectiveness were conducted for the whole population that started the treatment (ITT analysis—intent-to-treat). The general characteristics of the patients and the clinical symptomatology on entering the study were described using the mean values, the median values and the relative measurements of dispersion or the percentages. These characteristics were compared using the t-test or the chi-squared test, as appropriate.

The frequencies of the study parameters were compared and tested for statistical significance using the two-tailed chi-squared test and a significance level equal to 0.05 was considered.

The results for the pain scale (VAS) and for dyspareunia are given in Table 28 below.

TABLE 28

|  | T0 | T30 | T90 |
| --- | --- | --- | --- |
| Burning and dryness (VAS) | 7.82 | 3.21 | 2.72 |
| Dyspareunia | 2.96 | 1.18 | 1.15 |

The emulsion containing Nio-RCL was found to be significantly effective in improving the symptomatology of vaginal dryness.

The invention claimed is:
1. A topical composition, comprising:
(a) a water-based dispersion of niosomes; and
(b) at least one topically acceptable excipient,
wherein said niosomes comprise at least one plant extract and have a size lower than 500 nm, and wherein said niosomes are composed of amphiphilic molecules selected from the group consisting of a linear polyglycerol esterified with a saturated linear fatty acid, a branched polyglycerol esterified with a saturated linear fatty acid, a linear polyglycerol esterified with a mono-unsaturated linear fatty acid, a branched polyglycerol esterified with a mono-unsaturated linear fatty acid, and mixtures thereof.
2. The topical composition according to claim 1, wherein said niosomes have a diameter lower than 400 nm.
3. The topical composition according to claim 1, wherein said niosomes have diameter lower than 200 nm.
4. The topical composition according to claim 1, wherein said niosomes comprise at least one stabilizer or preservative selected from the group consisting of glycerine and a hydrosoluble natural antioxidant.
5. The topical composition according to claim 1, wherein said plant extract is an extract of a plant selected from the group consisting of Norway spruce, red clover, *ginkgo biloba*, and bilberry.
6. The topical composition according to claim 1, wherein said topical composition further comprises at least one excipient selected from the group consisting of: an emulsifier, a hydrating agent, a solvent, an emollient, a stabilizer, a viscosity modifier, a preservative, a lubricant, a sequestering agent, a chelating agent, a filler, a powder, a fragrance, a perfume, an absorbent, a dye, an opacifier, an antioxidant, a vitamin, a screening substance, a UV filter, an essential oil, a keratin-active substance, and an amino acid.

7. The topical composition according to claim 1, wherein said topical composition comprises said water-based dispersion of niosomes in an amount of from 1% to 5% by weight with respect to the total weight of said topical composition.

8. The topical composition according to claim 1, wherein said niosomes have diameter of 50 nm to 180 nm.

9. The topical composition according to claim 1, wherein said niosomes have diameter of 70 nm to 150 nm.

10. The topical composition according to claim 1, wherein said at least one plant extract is embedded in an aqueous compartment delimited by a double layer of said amphiphilic molecules.

11. The topical composition according to claim 1, which is in the form of a liquid or a semisolid cosmetic composition or contained in a medical device.

12. The topical composition according to claim 11, wherein said liquid composition is selected from the group consisting of a solution, emulsion, microemulsion, lotion, foam, milk, oil, foaming product, and suspension.

13. The topical composition according to claim 11, wherein said semisolid composition is selected from the group consisting of a cream, gel, balm, ointment, paste, cream gel, stick, and wax.

14. A water-based dispersion of niosomes,
wherein said niosomes comprise at least one plant extract and have a size lower than 500 nm, and wherein said niosomes are composed of amphiphilic molecules selected from the group consisting of a linear polyglycerol esterified with a saturated linear fatty acid, a branched polyglycerol esterified with a saturated linear fatty acid, a linear polyglycerol esterified with a mono-unsaturated linear fatty acid, a branched polyglycerol esterified with a mono-unsaturated linear fatty acid, and mixtures thereof.

15. A water-based dispersion of niosomes according to claim 14 comprising water in an amount of 30% to 40%, said amphiphilic molecules in an amount of 35% to 50%, glycerine in an amount of 10% to 20%, said at least one plant extract in an amount of 2% to 5%, and a hydrosoluble natural antioxidant in an amount of 1% to 6%, said amounts being expressed as percentage by weight with respect to the total weight of said water-based dispersion of niosomes.

16. The water-based dispersion of niosomes according to claim 14, wherein said niosomes have diameter of 50 nm to 180 nm.

17. The water-based dispersion of niosomes according to claim 14, wherein said niosomes have diameter of 70 nm to 150 nm.

18. A process for the preparation of a water-based dispersion of niosomes according to claim 14, comprising forming niosomes by hand shaking or ultrasonification of an aqueous mixture which comprises 35% to 50%, based on the weight of said aqueous mixture, of an amphiphilic compound selected from the group consisting of a linear polyglycerol esterified with a saturated linear fatty acid, a branched polyglycerol esterified with a saturated linear fatty acid, a linear polyglycerol esterified with a mono-unsaturated linear fatty acid, a branched polyglycerol esterified with a mono-unsaturated linear fatty acid, and mixtures thereof.

* * * * *